US012705740B2

(12) United States Patent
Martinez et al.

(10) Patent No.: US 12,705,740 B2
(45) Date of Patent: Aug. 11, 2026

(54) COMPUTER-BASED BODY PART ANALYSIS METHODS AND SYSTEMS

(71) Applicant: ICA AESTHETIC NAVIGATION GMBH, Frankfurt am Main (DE)

(72) Inventors: Carlos Martinez, Frankfurt (DE); Roman Goertelmeyer, Frankfurt (DE); Florian Velten, Wiesbaden (DE); Rainer Pooth, Bad Soden (DE)

(73) Assignee: ICA AESTHETIC NAVIGATION GMBH, Frankfurt am Main (DE)

( * ) Notice: Subject to any disclaimer, the term of this patent is extended or adjusted under 35 U.S.C. 154(b) by 195 days.

(21) Appl. No.: 18/561,088

(22) PCT Filed: May 20, 2022

(86) PCT No.: PCT/EP2022/063687
§ 371 (c)(1),
(2) Date: Nov. 15, 2023

(87) PCT Pub. No.: WO2022/243498
PCT Pub. Date: Nov. 24, 2022

(65) Prior Publication Data

US 2024/0265533 A1 Aug. 8, 2024

(30) Foreign Application Priority Data

May 20, 2021 (EP) .................................... 21174943

(51) Int. Cl.
*G06V 10/10* (2022.01)
*G06T 7/00* (2017.01)
(Continued)

(52) U.S. Cl.
CPC ............ *G06T 7/0012* (2013.01); *G06V 10/17* (2022.01); *G06V 10/764* (2022.01);
(Continued)

(58) Field of Classification Search
None
See application file for complete search history.

(56) References Cited

U.S. PATENT DOCUMENTS

2009/0257654 A1* 10/2009 Roizen ................ A45D 44/005 705/2
2018/0350071 A1 12/2018 Purwar et al.
(Continued)

FOREIGN PATENT DOCUMENTS

CN 112766019 A 5/2021

OTHER PUBLICATIONS

International Application No. PCT/EP2022/063687, International Search Report and Written Opinion, mailed Sep. 19, 2022.
(Continued)

*Primary Examiner* — Edward Park
(74) *Attorney, Agent, or Firm* — MARSHALL, GERSTEIN & BORUN LLP

(57) ABSTRACT

The present invention provides methods for determining a personal improvement potential of physiological characteristics of human faces or other body parts. This may involve determining an objective score of at least one physiological characteristic, in particular an attractiveness and/or youthfulness score, of the face of a human user. More specifically, the invention provides a computer-implemented body part analysis method. The method may comprise an image acquisition step, comprising obtaining one or more digital images of at least one body part of a user, in particular the user's face, captured by an image capturing device. The method may further comprise an image processing step, comprising detecting one or more biometric parameters of the at least one body part in the captured one or more digital images. Still further, the method may comprise an evaluation step, comprising determining a score for each of one or more
(Continued)

physiological characteristics of the at least one body part based on the detected one or more biometric parameters.

15 Claims, 6 Drawing Sheets

(51) Int. Cl.
*G06V 10/764* (2022.01)
*G06V 10/77* (2022.01)
*G06V 10/82* (2022.01)
*G06V 40/16* (2022.01)
*G06V 40/60* (2022.01)
*G16H 20/30* (2018.01)

(52) U.S. Cl.
CPC .......... *G06V 10/7715* (2022.01); *G06V 10/82* (2022.01); *G06V 40/165* (2022.01); *G06V 40/171* (2022.01); *G06V 40/60* (2022.01); *G16H 20/30* (2018.01); *G06T 2207/10024* (2013.01); *G06T 2207/20081* (2013.01); *G06T 2207/20084* (2013.01); *G06T 2207/30088* (2013.01); *G06T 2207/30201* (2013.01)

(56) References Cited

U.S. PATENT DOCUMENTS

2018/0352150 A1 12/2018 Purwar et al.
2021/0012097 A1* 1/2021 Velthuis ............... G06V 40/172
2021/0015241 A1 1/2021 Kuang

OTHER PUBLICATIONS

Liao et al., Deep rank learning for facial attractiveness, 2017 4th IAPR Asian Conference on Pattern Recognition (ACPR), IEEE, pp. 565-570 (Nov. 2017).
Xu et al., Facial attractiveness prediction using psychologically inspired convolutional neural network (PI-CNN), 2017 IEEE International Conference on Acoustics, Speech and Signal Processing, pp. 1657-1661 (Mar. 2017).

* cited by examiner

Fig. 1
Lighting
Face Position
Orientation
Eyes
Facial Expression
1.Neutral

COMPUTER-BASED BODY PART ANALYSIS METHODS AND SYSTEMS

TECHNICAL FIELD

The present invention generally relates to the field of computer vision, more specifically to the field of body part detection, such as face detection, and even more specifically to an accurate, efficient and objective method for predicting attractiveness and/or youthfulness in digital images.

BACKGROUND ART

Computer vision is among the most promising yet challenging fields for modern-day machine learning techniques. Generally speaking, computer vision refers to techniques how computers can gain higher-level understanding from digital images or videos. Computer vision tasks include methods for acquiring, processing, analyzing and understanding digital images, and the extraction of high-dimensional data from the real world to produce numerical or symbolic information, e.g. in the form of decisions.

One particular subdomain of computer vision is object detection, in particular face detection. Exemplary applications for face detection techniques include facial recognition (e.g. matching a human face from a digital image against a database of faces, typically to authenticate the human), photography (e.g. to use face detection for autofocus), or automated lip reading (e.g. enabling a computer program to determine who is speaking in a video conference).

Yet another application for face detection relates to techniques for determining physiological characteristics of the user's face in a digital image, e.g. characteristics such as the skin firmness, the skin smoothness, the skin elasticity, the perceived age, and even higher-level characteristics such as the attractiveness of the user.

For example, the article "A new humanlike facial attractiveness predictor with cascaded fine-tuning deep learning model" (J. Xu et al., 8 Nov. 2015, arXiv:1511.02465 [cs.CV]) proposes a deep leaning method to address the facial attractiveness prediction problem. The method constructs a convolutional neural network of facial beauty prediction using a deep cascaded fine-turning scheme with face inputting channels, such as the original RGB face image, the detail layer image, and the lighting layer image. Using a CNN model of deep structure, large input size and small convolutional kernels, a prediction correlation of 0.88 could be achieved according to the article.

As another example, WO 2019/136354 A1 proposes a computer system in which an image is accepted by one or more processing circuits from a user depicting the user's facial skin. Machine learning models stored in one or more memory circuits are applied to the image to classify facial skin characteristics. A regimen recommendation is provided to the user based on the classified facial skin characteristics. Further examples of methods that provide personalized product recommendations based on pictures of a user's face can be found in WO 2008/057577 A1 and WO 2017/083576 A1.

One way of implementing face detection is by using an application programming interface such as the Face++ API, an AI-based open computer vision platform. Face++ detects and locates human faces within an image and returns high-precision face bounding boxes. Exemplary algorithms for face recognition include LBPH, the Fisherface method or PCA.

Furthermore, some companies in the skin care industry provide web applications which are able to measure optical skin age, skin tightness and skin evenness on standardized selfie images and return results with product recommendations. Examples include the Nivea "Skin Guide" and the L'Oreal "Skin Genius".

Betaface is a face recognition software for media-related companies. It returns details from an uploaded picture, including age, expression, beard, race, glasses, beard and hair color, mustache, chin size, eyes color, eyes position, eyebrows color/thickness/position, hair length, head shape, mouth height and shape, nose shape and size, teeth and some others. It is also able to find similar faces within >40.000 celebrities or within Wikipedia's database. Facial recognition with similar purposes is also used by other software including face comparison tools (Google Reverse Image Search, TwinsOrNot.net, FindFace/VK.com, Pictriev, PicWiser) which compare an uploaded photo with those found on the web or which compare two uploaded photos and to determine how much two faces resemble).

Furthermore, photo-editors (e.g. Adobe Photoshop) edit and compose raster images in multiple layers and typically support masks, alpha compositing and several color models. However, this is far from any objective measure.

Lastly, even special photographic equipment is needed by other facial measures of aesthetic features. In this context, facial areas typically have to be manually outlined before the analyses to finally lead to a customized report on wrinkles, pores, oiliness, evenness, vascularization and/or pigmentation, thereby serving to demonstrate the outcome of minimal-invasive or surgical treatments by image simulation during the pre-Op consultation. One such example is LifeViz QuantifiCare.

However, further improvements of the prior art techniques are possible, in particular in terms of face detection accuracy and usability of the known systems.

It is therefore the technical problem underlying the present invention to provide techniques for improved face detection and analysis of the physiological characteristics of a user's face.

SUMMARY OF THE INVENTION

The invention is defined in the independent claims. In one embodiment, a computer-implemented body part analysis method is provided. The method may comprise an image acquisition step, comprising obtaining one or more digital images of at least one body part of a user, in particular the user's face, captured by an image capturing device. The method may further comprise an image processing step, comprising detecting one or more biometric parameters of the at least one body part in the captured one or more digital images. Still further, the method may comprise an evaluation step, comprising determining a score for each of one or more physiological characteristics of the at least one body part based on the detected one or more biometric parameters.

Accordingly, the method provides a novel and unique image processing technique. The method takes as input digital images, in particular photographs, of a user's face, neckline, hand or other body part(s), and therefore operates on measurement data having a direct link with physical reality. One or more biometric parameters, i.e. technical/physical properties, of the at least one body part are extracted from the input images. The output of the method is an objective estimation of the score of one or more physiological characteristics of the at least one body part. As used herein, the term "body part" may refer, without limitation, to the head, face, neck, shoulder, arm, elbow, forearm, hand, wrist, thigh, knee, leg, ankle, foot, toe, breast, buttock, pelvis, or combinations thereof.

One possible application of the techniques disclosed herein relates to the assessment of physiological characteristics of the human face. Therefore, in the following the face will oftentimes be used as an illustrative non-limiting example for a body part. However, it shall be understood that the techniques disclosed herein apply equally to any kind of body part and shall not be limited to the face. The one or more biometric parameters may be selected from the group comprising skin texture (in particular relating to the nose, upper lip, suborbital area and/or cheek), wrinkles (in particular relating to the eye lids, glabella, infraorbital area, chin, crow's feet, marionette wrinkles, nasolabial area, upper lip, radial area and/or forehead), color (in particular relating to haemoglobin, luminance and/or melanin), volume (in particular relating to the cheek(s), eye groove and/or midface region), proportions (in particular relating to the distance between nose, upper lip and/or lower lip, the chin width, the lip width and/or the V-shape) and/or geometry (in particular relating to the eyebrow arch). This way, the method is particularly versatile and allows estimating the desired physiological characteristics based on a given selection of biometric features which is suitable for the task at hand, in particular depending on the expected images that are to be processed.

The one or more biometric parameters may comprise at least one phenotypical parameter and/or at least one modifiable parameter. Accordingly, this aspect provides a grouping of the biometric parameters in non-modifiable and modifiable parameters, and allows to define suitable treatments for enhancing the modifiable parameters.

The one or more physiological characteristics may comprise the skin firmness, the skin smoothness, the skin elasticity, the perceived age, the attractiveness and/or the youthfulness of the user. Accordingly, the method assign scores to one or more objectively measurable characteristics and therefore provide reliable and accurate results.

In one aspect of the present invention, the image processing step may comprise detecting a (single) biometric parameter of the at least one body part, and the evaluation step may comprise determining a score for one (single) physiological characteristic. The biometric parameter may represent a biometric deficiency and the score may represent a severity grading of the biometric deficiency. Accordingly, this aspect of the invention may serve for providing a digital aesthetic scale. As an illustrative and non-limiting example, the method may be used to grade the severity of the glabella wrinkle on a scale of e.g., 0 to 4 in a particularly objective manner.

In one aspect of the invention, the one or more digital images obtained in the image acquisition step may comprise an image which shows the user's face in a predetermined orientation, such as a frontal view, a profile view, a lateral view and/or an oblique view. In case two or more digital images are obtained in the image acquisition step, the two or more digital images may comprise at least two digital images with the same orientation and/or at least two digital images with different orientations.

A frontal view may serve for improving a detection and/or evaluation of the general geometry of the user's face and/or one or more biometric characteristics, such that the detection may require a minimum amount of input images.

A profile view, a lateral view and/or an oblique view may serve for improving a detection and/or evaluation of the chin line, jaw line, temples and/or cheeks of the user's face, which may lead to a more elaborate face analysis. Different angles may be used in such views. As will be explained further below.

In one aspect of the invention, the one or more digital images obtained in the image acquisition step may comprise an image which shows the user's face with a predetermined facial expression, such as a neutral facial expression and/or a non-neutral facial expression. The non-neutral facial expression may be a smiling facial expression and/or a frowning facial expression. In case two or more digital images are obtained in the image acquisition step, the two or more digital images may comprise at least two digital images with the same facial expression and/or at least two digital images with different facial expressions.

A neutral facial expression may serve for improving a detection and/or evaluation of the general geometry of the user's face and/or one or more biometric characteristics, such that the detection and/or evaluation may require a minimum amount of input images.

Using digital images with different facial expressions may further improve the face analysis, because non-neutral facial expressions may emphasize certain one or more biometric characteristics of the user's face which are less visible in the neutral view. In particular, a smiling facial expression and/or a frowning facial expression may make wrinkles in the user's face more visible, leading to a better detectability of the wrinkle depth and/or severity and/or other parameters.

The above aspects relating to the orientation and facial expression may be freely combined. Thus, aspects of the present invention may provide for any combination of digital images with any combination of orientations and/or facial expressions. In one aspect of the method, the one or more digital images may comprise a first digital image. The first digital image may be a digital image with a first orientation and/or with a first facial expression. The one or more digital images may comprise a second digital image. The second digital image may be a digital image with a second orientation and/or with a second facial expression. The one or more digital images may comprise a third digital image. The third digital image may be a digital image with a third orientation and/or with a third facial expression. The one or more digital images may comprise a fourth digital image. The fourth digital image may be a digital image with a fourth orientation and/or with a fourth facial expression. The one or more digital images may comprise a fifth digital image. The fifth digital image may be a digital image with a fifth orientation and/or with a fifth facial expression. The one or more digital images may comprise a sixth digital image. The sixth digital image may be a digital image with a sixth orientation and/or with a sixth facial expression. The one or more digital images may comprise a seventh digital image. The seventh digital image may be a digital image with a seventh orientation and/or with a seventh facial expression. The one or more digital images may comprise an eighth digital image. The eighth digital image may be a digital image with an eighth orientation and/or with an eighth facial expression. The one or more digital images may comprise a nineth digital image. The nineth digital image may be a digital image with a nineth orientation and/or with a nineth facial expression. The one or more digital images may comprise a tenth digital image. The tenth digital image may be a digital image with a tenth orientation and/or with a tenth facial expression. The one or more digital images may comprise one or more further digital images in excess of ten digital images. The one or more further digital image may be one or more digital images with one or more respective further orientations and/or with one or more respective further facial expressions.

Note that in some aspects of the invention, the designation "first digital image", "second digital image", "third digital image", etc. as well as similar designations may imply a sequence in which the digitial images are taken. However, in other aspects of the invention, such designations do not imply a sequence in which the digital images are taken, but rather serve to distinguish one image from the other in the disclosure provided herein.

The first digital image may be a first digital image with a frontal view of the user's face, preferably with a neutral facial expression. This way, the general geometry of the user's face and several relevant biometric characteristics may be detected with a minimum amount of input images.

The one or more digital images may further comprise a second digital image with a lateral view of the user's face, preferably with a neutral facial expression. The lateral view improves the detection and/or evaluation of the chin line, jaw line, temples and/or cheeks of the user's face, eventually leading to a more elaborate face analysis. The second image with the lateral view, or more generally speaking, any digital image with a lateral view of the user's face, may show the user's face at an angle which is not 0 degrees (which would be a frontal view) and/or which is not 90 degrees (which would be a full profile view). Preferably, the lateral view may show the user's face approximately at an angle between 5 to 85 degrees, more preferably approximately at an angle between 10 to 80 degrees, more preferably approximately at an angle between 20 to 70 degrees, more preferably approximately at an angle between 30 and 60 degrees, more preferably approximately at an angle between 40 and 50 degrees, and still more preferably at approximately 45 degrees, which is an optimal trade-off between chin line detectability and user convenience, since the user can still see himself/herself while taking the picture.

Still further, the one or more digital images may also comprise a third digital image, preferably with a frontal view of the user's face, with a facial expression different from the facial expression in the first digital image. Using images with different facial expressions may further improve the face analysis, because non-neutral facial expressions may emphasize certain biometric characteristics of the user's face which are less visible in the neutral view. In particular, the facial expression in the third digital image may be a smiling facial expression or a frowning facial expression, which may make wrinkles in the user's face more visible, leading to a better detectability of the wrinkle depth and/or severity.

In a particularly elaborated scenario, the facial expression in the third digital image may be a smiling facial expression and the one or more digital images may further comprise a fourth digital image, preferably with a frontal view of the user's face, with a frowning facial expression. Accordingly, in this scenario the one or more digital images which serve as the input of the face analysis comprise (or may even consist of) four digital images with the mentioned characteristics, which may enable a particularly precise detection of biometric features.

In one practical aspect of the invention, a computer-implemented face analysis method is provided, comprising: an image acquisition step, comprising obtaining at least three digital images of a user's face, comprising: a first digital image with a frontal view of the user's face with a neutral facial expression; a second digital image with a lateral view of the user's face with a neutral facial expression; and a third digital image with a frontal view of the user's face with a smiling facial expression or a frowning facial expression; an image processing step, comprising detecting one or more biometric parameters of the face in the captured at least three digital images; and an evaluation step, comprising determining a score for each of one or more physiological characteristics of the based on the detected one or more biometric parameters.

In one practical aspect of the invention, a computer-implemented face analysis method is provided, comprising: an image acquisition step, comprising obtaining four digital images of a user's face. The four digital images may be obtained by interactively guiding the user through a series of four photographs using an image capturing device. The four digital images include: a digital image with a frontal view of the user's face with a neutral facial expression; a digital image with a frontal view of the user's face with a smiling facial expression; a digital image with a frontal view of the user's face with a frowning facial expression; and a digital image with a lateral view of the user's face with a neutral facial expression, wherein, optionally, the lateral view shows the user's face approximately at an angle between 20 and 70 degrees; an image processing step, comprising detecting one or more biometric parameters of the at least one body part face in the captured one or more four digital images; and an evaluation step, comprising determining a score for each of one or more physiological characteristics of the at least one body part face based on the detected one or more biometric parameters.

In another aspect of the method, the image acquisition step may further comprise providing instructions to the user for adjusting the lighting, the position of the user's face relative to the image capturing device, the distance of the user's face to the image capturing device and/or the orientation of the user's face relative to the image capturing device. The step of providing instructions may comprise displaying text, symbols and/or visual indications, such as one or more leading lines, on a display associated with the image capturing device. These aspects assist the user in performing the image obtaining task by means of a continued and/or guided human-machine interaction process and result in input images of higher quality.

In one aspect of the invention, the one or more digital images may be captured using a mobile device, in particular a smartphone. Alternatively, the one or more digital images may be captured using an electronic device incorporated in a smart mirror.

In yet another aspect of the invention, the evaluation step may be performed using at least one statistical classifier which is configured to map one or more biometric features to a score for one or more physiological characteristics of the at least one body part. In particular, the at least one statistical classifier may be configured to map a predefined number, such as three or five, biometric parameters to a score of the attractiveness and/or youthfulness of the user's face. Because of the unique characteristics of the statistical classifier of embodiments of the invention, only comparatively few biometric parameters have to be extracted from the input images in order to arrive at a high quality and in particularly objective estimation of the physiological characteristic(s), such as attractiveness and/or youthfulness.

In one aspect, a first statistical classifier may be configured to map a first predefined set of biometric features to an attractiveness score and a second statistical classifier may be configured to map a second predefined set of biometric features to a youthfulness score. The first and second predefined sets of biometric features may overlap partially. The first and second statistical classifiers may be provided as separate models, or as a combined model. Accordingly, (at least partly) different predictors may be used for estimating attractiveness and youthfulness.

Preferably, the first predefined set may comprise at least one biometric parameter relating to color, in particular relating to haemoglobin, luminance and/or melanin, and the second predefined set may comprise at least one biometric parameter relating to wrinkles, in particular relating to the eye lids, glabella, infraorbital area, chin, crow's feet, marionette wrinkles, nasolabial area, upper lip, radial area and/or forehead. Accordingly, findings of the clinical studies underlying embodiments of the invention may be directly encoded in the implementation of the statistical classifier, thereby leading to very accurate estimations with only a relatively simple computational model.

The statistical classifier may have been trained using a training data set comprising a plurality of images of human faces, a selection of one or more biometric parameters and/or a score for each of one or more physiological characteristics. Furthermore, the statistical classifier may be trained and/or pre-trained using a publicly available data set, such as SCUT-FBP. Pre-training the classifier greatly reduces the amount of training data sets needed to adapt the classifier to the final problem domain.

Preferably, the statistical classifier is an artificial neural network, in particular a deep neural network.

In yet another aspect, the method may further comprise the step of displaying the one or more scores on a display associated with the image capturing device. For example, the display may be comprised in the same apparatus as the image capturing device, or the display may be more indirectly associated with the image capturing device, e.g. when it is part of a remote computer connected over a network. The method may also comprise the step of recommending, to the user, one or more treatments to improve the score associated with the one or more physiological characteristics. The one or more recommended treatments may be ranked by their expected or predicted impact on improving the score associated with the one or more physiological characteristics. This way, the user can be provided with suitable recommendations, in particular personalized and/or individualized treatment plans, for improving his/her physiological characteristics. In one aspect, the one or more treatments are selected such as to optimize a personalized maximum improvement potential relative to one or more individual biometric parameters or in total.

Furthermore, the method may comprise the step of displaying an estimated change of the one or more scores after application of the recommended one or more treatments. Accordingly, the user is enabled to validate the likely impact of a given treatment on his/her physiological characteristics, and can pick the most appropriate one, thereby avoiding sub-optimal or even harmful physiological treatments of the user's face.

The invention also provides an apparatus comprising means for carrying out any of the methods disclosed herein, as well as a computer program comprising instructions which, when the program is executed by a computer, cause the computer to carry out any of the methods disclosed herein. A computer-readable storage medium is also provided, comprising instructions which, when executed by a computer, cause the computer to carry out any of the methods disclosed herein.

Moreover, the invention concerns a training data set for training the statistical classifier disclosed herein, comprising a plurality of images of human faces, a selection of one or more biometric parameters and/or a score for each of one or more physiological characteristics. Lastly, a method of training the statistical classifier using the training data set is provided.

BRIEF DESCRIPTION OF THE DRAWINGS

The disclosure may be better understood by reference to the following drawings.

DESCRIPTION OF EMBODIMENTS

Figure 1:
FIG. 1: A user interface of a smartphone application for guiding the user during the image acquisition process in accordance with embodiments of the invention.

Embodiments of the present invention generally provide methods for determining a personal improvement potential of physiological characteristics of human faces. This may involve determining an objective score of at least one physiological characteristic, in particular an attractiveness and/or youthfulness score, of the face of a human user. Certain embodiments may use using machine learning techniques using models which embody complex domain knowledge about the biometric parameters of human faces and their impact on the physiological characteristics of interest.

In certain embodiments, one or more conventional photographs of the user's face are sufficient for accurately determining the at least one physiological characteristic and/or the associated score. No 3D scan is necessary. Accordingly, the technique may be embodied in a computer program forming an application ("app") for an electronic user equipment, such as a smartphone, tablet, or the like, and the user may take respective "selfies" to provide the photographs. Alternatively, the application may be incorporated in a smart and/or electronic mirror. In one particular embodiment, the user is prompted to take a series of specific photographs, as will be explained in more detail further below.

In certain embodiments, the attractiveness and/or youthfulness score may take into account and/or be based on biometric parameters such as proportions, wrinkles and/or pigmentation. However, embodiments of the invention may use all or any subset of a variety of biometric parameters derivable from the one or more input images, as will be explained in more detail further below. The relevant biometric parameters have been developed in complex experiments and clinical studies, and their ideal values (in terms of their impact on the physiological characteristics) have been identified. In particular, different sets of predictors (i.e. biometric parameters) for attractiveness and youthfulness have been identified. The resulting model allows for a particularly fast and resource-saving, yet accurate calculation of the physiological characteristic(s) from relatively simple photographs of the user's face.

Based on the determined score, one or more products and/or treatments may be recommended to the user to improve the score. Furthermore, an estimated change of the score after application of the one or more products and/or treatments may be displayed to the user. Accordingly, embodiments of the invention may determine individual deficient biometric parameters (so-called landmarks) and may determine the individual improvement potential for individual landmarks or in total. Embodiments may then provide an individualized and/or prioritized treatment plan to the user for improving his/her physiological characteristic (s).

In one embodiment, Facial attractiveness may be immediately analyzed online by after uploading one or more selfie pictures of the face. Embodiments of the invention may split the face automatically into various regions, and a number of facial proportions of facial characteristics such as wrinkles, of local and global homogeneity, of rough and fine skin surface textures and/or colors may be measured in all or at least part of the facial areas. These variables may be transformed into local and/or global interval- or ordinal-scaled features such as a volume score, wrinkle scores, color indices, various homogeneity scores and/or different indices for symmetry and/or geometry. One unique property of certain embodiments of the invention are global indices for attractiveness and/or youthfulness which are calculated from the corresponding variables. The algorithms behind those local and regional features and the mentioned unique global indices are validated by subjective assessments using a set of lay people and experts.

Smartphone Application

Embodiments of the invention provide a computer program executable on a mobile device, in particular a smartphone (a so-called "application" or "app") configured to perform a holistic face analysis and/or provision of personalized treatment plans. Apparently, a smartphone is only one possible example of a mobile device, whereas the techniques disclosed herein are equally applicable to other sorts of mobile devices. Moreover, while the smartphone/mobile device embodiment is primarily targeted to end consumers, also other use cases are possible. For example, in a medical use case, the techniques disclosed herein may operate based on one or more images taken by the user or a third party, while the image processing and analysis is performed by a separate computer system, e.g. a cloud-based system.

In the following, an exemplary user journey through the application will be described with reference to the embodiment shown in FIGS. 1-5. It shall be appreciated that the exact sequence of the described steps is not mandatory, and that certain steps may be omitted in different embodiments.

Initially, the application may prompt the user to provide general user information (not shown in FIGS. 1-5). This may include prompting the user to provide information for identifying the user, such as a name and/or an email address. The application may provide an option to create a user account, which may involve prompting the user to create a password. Next, the application may prompt the user to provide his/her biological age and/or gender, which may be advantageous for deriving scientifically sound recommendations. The information may be obtained by any suitable input means on a graphical user interface provided by the application, such as text boxes, drop down menus, buttons and other control elements.

Then, the application may enter an image acquisition phase. This may involve prompting the user to provide one or more images of the user's face as the input to the subsequent face analysis. In a preferred embodiment, the application prompts the user to capture one or more digital images of the user's face, i.e. to take photographs, using an image capturing device, in particular the camera of the mobile device which also executes the application. This way, the user may provide the input images by way of taking "selfies". This is not only particularly convenient, but also adds a certain lifestyle element to the application. In an alternative realization, the application may execute on a computing device incorporated in an apparatus comprising a mirror (conventionally referred to as "smart mirror"), which may allow performing the face analysis e.g. regularly such as every morning, in the user's bathroom.

FIG. 1 illustrates an exemplary user interface for guiding the user to take a suitable image of the user's face. As can be seen, the application may provide visual instructions to the user for how to take a high-quality input image. These visual instructions may include displaying a bounding ellipse, circle, box, or the like and/or one or more guiding lines to enable the user to properly position the face relative to the camera. The visual instructions may further include one or more indicators for indicating whether the level of lighting, the face positioning and/or the face orientation is appropriate. These visual instructions and/or indicators may interactively change in real-time as the user moves the face in front of the camera, thereby assisting the user in performing the taking of one or more images/photographs by means of a continued and/or guided human-machine interaction process.

In a preferred embodiment, the application interactively guides the user through a series of photographs. FIG. 1 shows an example in which a photograph with a neutral face expression is requested by the application. In one particular embodiment, the application prompts the user to take exactly four photographs: neutral expression, smiling expression, angry expression, and in a profile view, ideally at an angle of approximately 45 degrees with respect to the camera. However, other angles may be used, such as an angle between 20 and 70 degrees, between 30 and 60 degrees, or generally an angle of approximately 20, 25, 30, 35, 40, 45, 50, 55, 60, 65 or 70 degrees. The user may be prompted to take the pictures in the mentioned sequence, although this is not absolutely necessary. Experiments have shown that a corresponding set of four input images with the mentioned face expressions and/or orientations produces input data for the face analysis with sufficient quality while at the same time requiring only a minimum of user involvement during the production of the images. However, other sets of input images may be used in embodiments of the invention. For example, one embodiment may include two digital images, a first one with a frontal view (which allows detecting the general geometry of the face and several relevant biometric parameters) and a second one with a lateral view of the user's face (which allows detecting the chin line). Moreover, a third image may be used with a non-neutral facial expression, such as smiling or frowning, to further improve the visibility of certain biometric parameters such as wrinkles.

Once the required input images have been acquired, the application may perform image processing to detect one or more biometric parameters of the user's face in the captured one or more digital images. To this end, the image processing may be performed directly on the device executing the application or alternatively, the application may send the acquired images over a network to a server which then performs the image processing and sends the results back to the application.

The detected biometric parameters may include parameters associated with the skin (in particular relating to the nose, upper lip, suborbital area and/or cheek), wrinkles (in particular relating to the eye lids, glabella, infraorbital area, chin, crow's feet, marionette wrinkles, nasolabial area, upper lip, radial area and/or forehead), color (in particular relating to haemoglobin, luminance and/or melanin), volume (in particular relating to the cheek(s), eye groove and/or midface region), proportions (in particular relating to the distance between nose, upper lip and/or lower lip, the chin width, the lip width and/or the V-shape) and/or geometry (in particular relating to the eyebrow arch).

Extracting features, such as the one or more biometric parameters, from the input images may involve various face recognition algorithms. It shall be understood that such image processing may require considerable computing power and thus a trade-off may be taken between the accuracy of the face recognition and the required processing resources. In particular, more, less or other parameters may be used in embodiments of the invention depending on the needed accuracy of the face analysis, and a detailed list of feasible biometric parameters will be provided further below.

Figure 2:
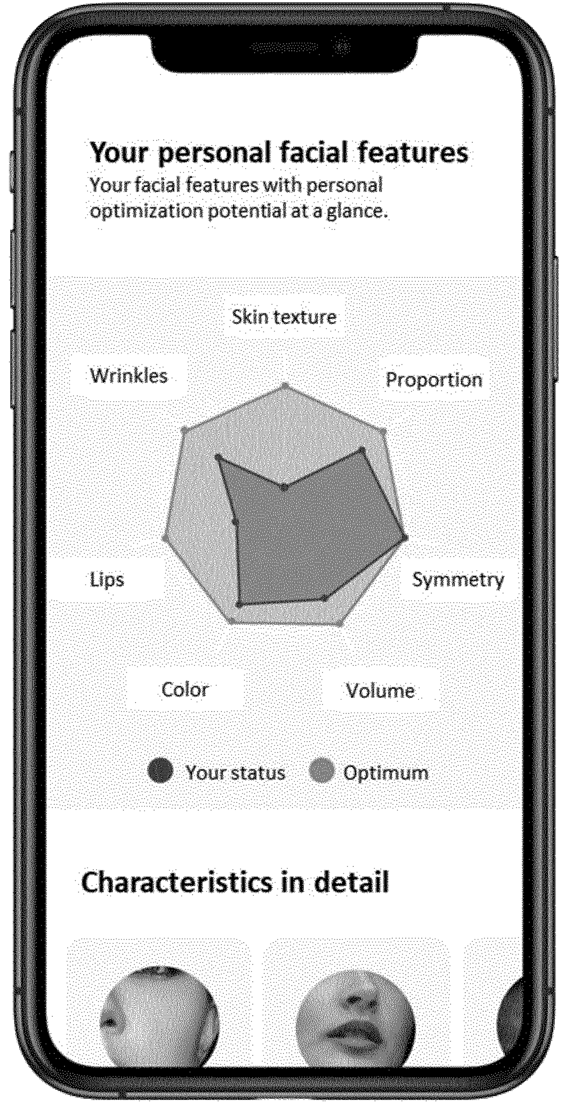
FIG. 2: User interfaces of a smartphone application for analyzing individual biometric parameters and physiological characteristics of the user in accordance with embodiments of the invention.
Figure 2:
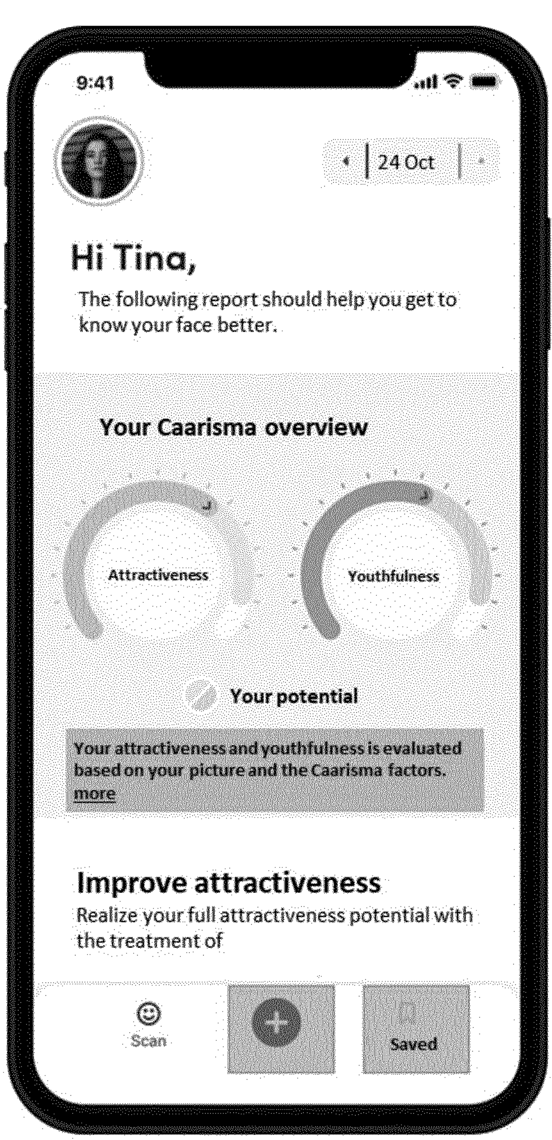

In some embodiments, values of the detected biometric parameters may be combined into more complex, higher-level biometric parameters, and eventually combined into one or more representative physiological characteristics of the user's face. A score may be assigned to each of the one or more physiological characteristics. The scoring may be performed locally on the user device or on a remote server. In the embodiment shown on the left-hand side of FIG. 2, the physiological characteristics comprise skin texture, proportion, symmetry, volume, color, lips and/or wrinkles, leading to an elaborated assessment of the user's face. In other embodiments, the physiological characteristics may be even more combined ones, such as a single score for attractiveness and/or a single score for youthfulness, as shown on the right-hand side of FIG. 2. As also shown in FIG. 2, not only the physiological characteristics and/or their scores may be displayed, but also an optimal or target value.

Figure 3:
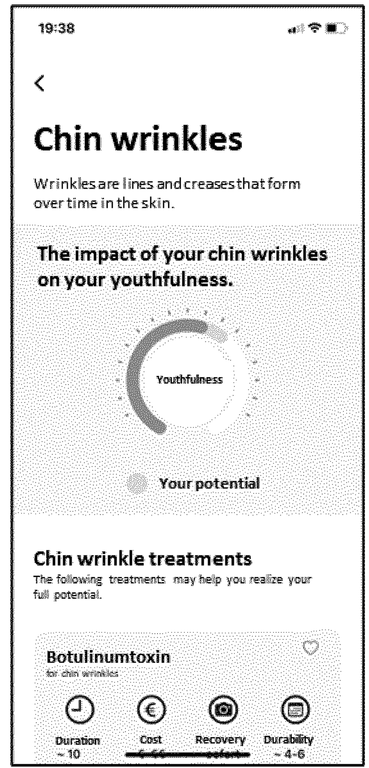
FIG. 3: User interfaces of a smartphone application for displaying deficient biometric parameters for an individual, corresponding improvement potential and recommended treatment options for realizing the improvement potential in accordance with embodiments of the invention.
Figure 3:
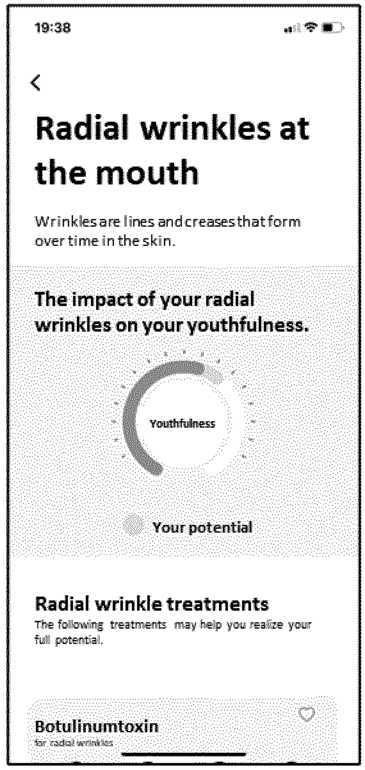
Figure 3:
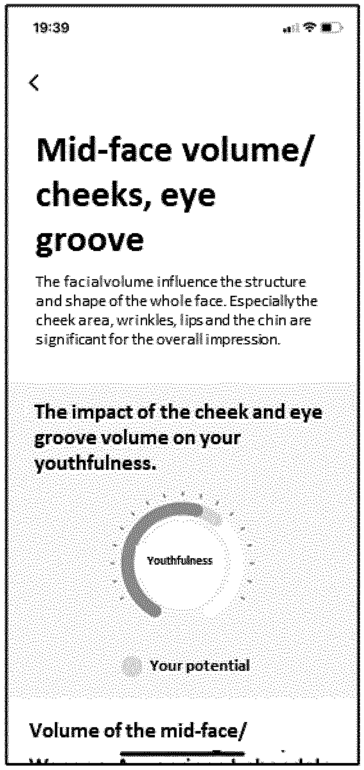
Figure 3:
Figure 3:
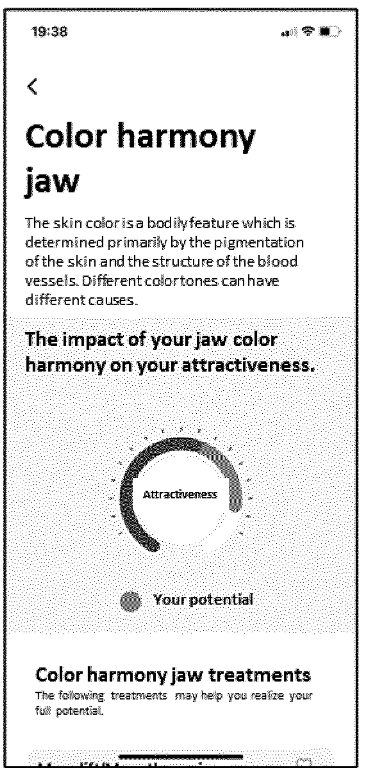
Figure 3:
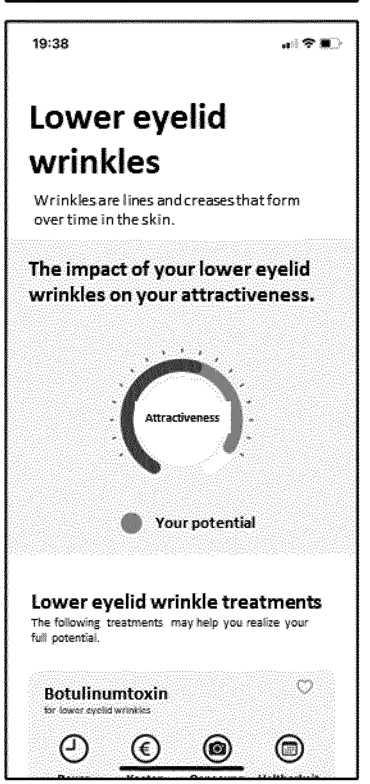
Figure 4:
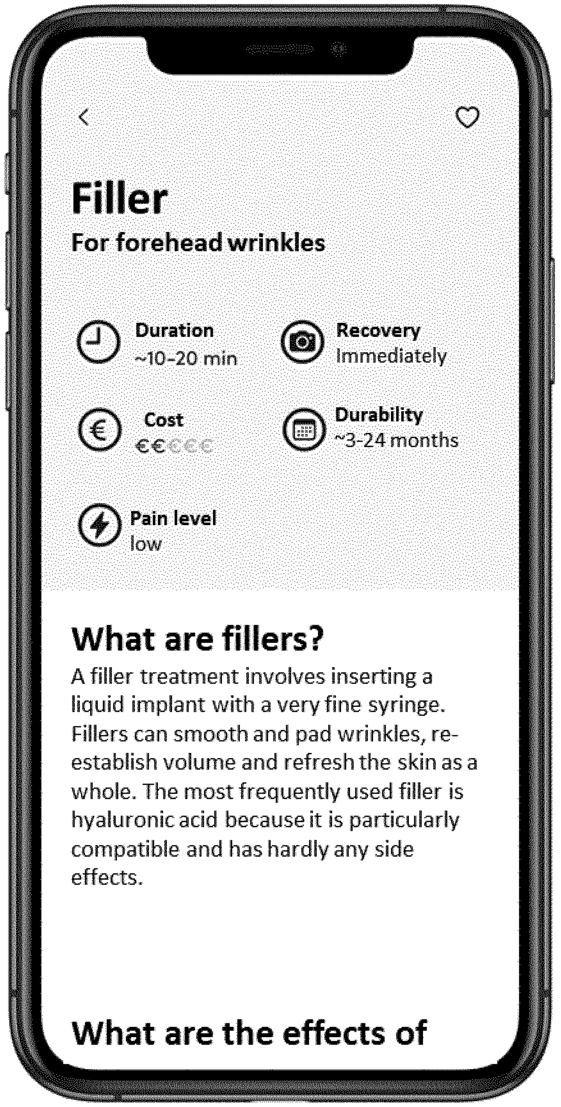
FIG. 4: User interfaces of a smartphone application for recommending treatment options and experts for carrying out the treatments in accordance with embodiments of the invention.
Figure 4:
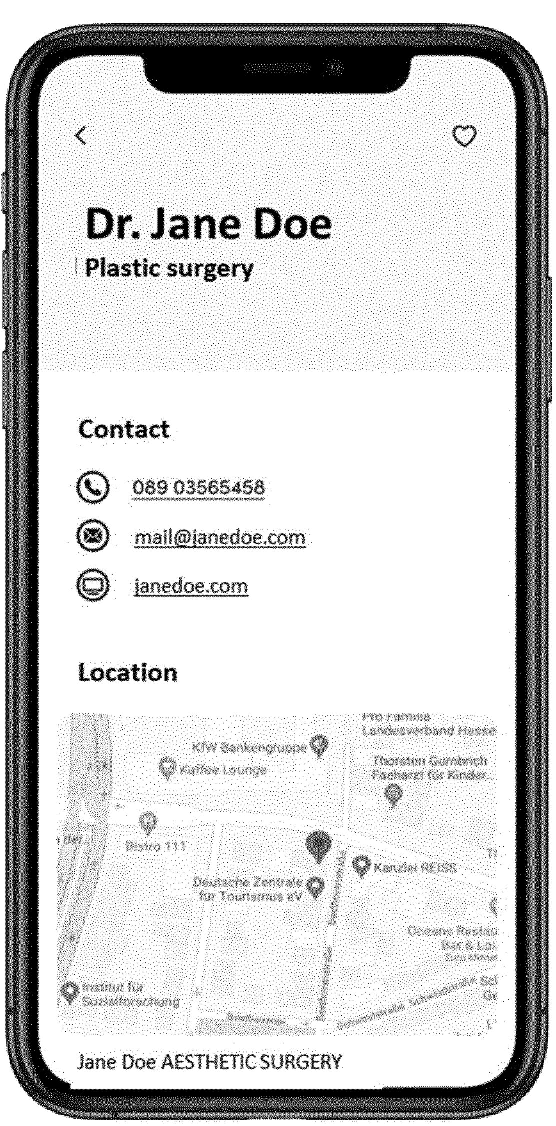

FIG. 3 illustrates examples of individual biometric parameters (in the example: chin wrinkles, radial wrinkles at the corner of the mouth, mid-face volume/cheeks, eye rim, forehead wrinkles, color harmony of the jaw, lower eyelid wrinkles) and their respective score for an exemplary individual. Also shown is the personal improvement potential for each displayed biometric parameter, i.e. the degree to which the respective biometric parameter could be improved using suitable measures. To this end, suitable treatments are also displayed in FIG. 3. Accordingly, the application may recommend one or more treatments to the user to improve the score associated with the one or more biometric parameters and/or physiological characteristics. As another example, as illustrated in the embodiment of FIG. 4, if the user has a potential to improve his/her forehead wrinkles, the application may display a recommendation to apply a filler treatment, and may provide relevant information associated with this treatment (see the left-hand side of FIG. 4). Moreover, the application may recommend competent experts for applying the one or more treatments, as shown in the right-hand side of FIG. 4.

In certain embodiments, personalized and/or individualized treatment plans may be derived from the face analysis results and recommended to the user. Generally, a treatment plan may comprise a plurality of selected treatment options. For example, it may comprise certain specific treatment options for improving youthfulness and/or other specific treatment options for improving attractiveness (e.g. three treatment options each).

Figure 5:
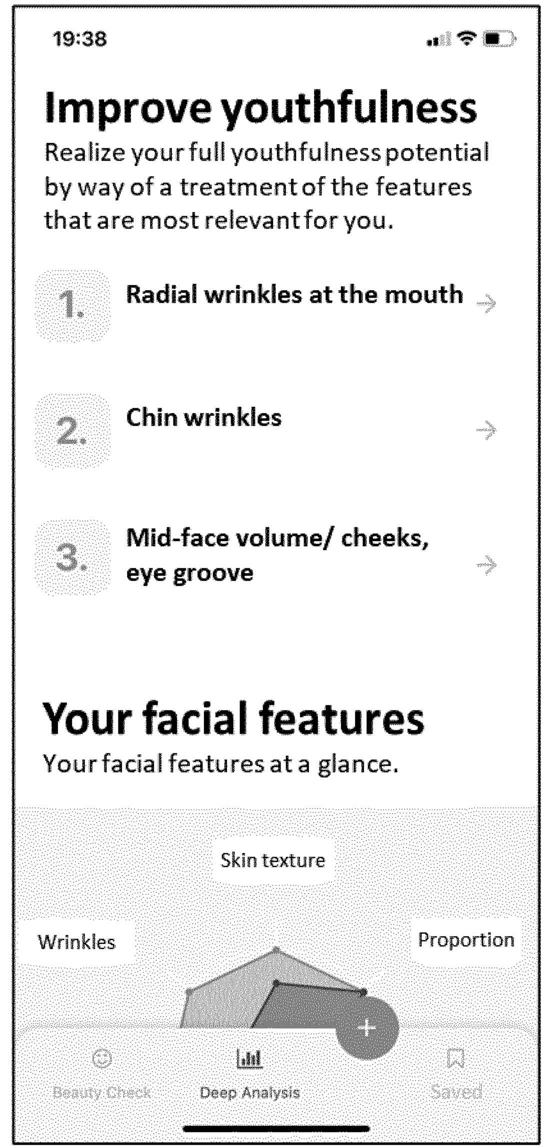
FIG. 5: User interfaces of a smartphone application for displaying the impact of selected biometric parameters on attractiveness and/or youthfulness in accordance with embodiments of the invention.
Figure 5:
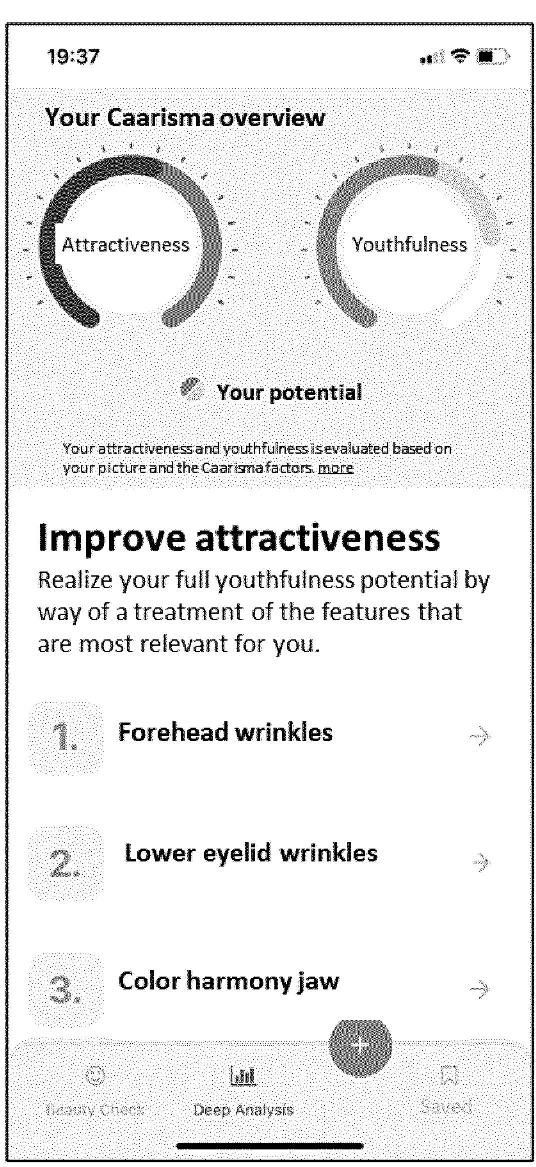

Examples are illustrated in FIG. 5. As can be seen on the left-hand side, the application displays to the user the three biometric parameters that have the greatest impact on youthfulness (in the example: radial wrinkles at the corner of the mouth, chin wrinkles and mid-face volume/cheeks, eye rim). On the right-hand side of FIG. 5, the application displays the three biometric parameters that have the greatest impact on attractiveness (in the example: forehead wrinkles, lower eyelid wrinkles and color harmony of the jaw).

Model Derivation

In order to provide a particularly accurate and/or objective assessment of the physiological characteristics of the user's face, a model was developed in the context of clinical studies to identify and quantify objective predictors for facial attractiveness as well as objective predictors for youthfulness as follows:

A series of standardized portrait photographs was rated by experts in terms of the attractiveness/youthfulness of the depicted faces.

The photographs were then digitally characterized with several hundreds of individual (biometric) parameters, such as without limitation horizontal eye distance, vertical distance between upper lip and nose, forehead wrinkles, chin wrinkles, skin homogeneity, skin tone, etc. In one variation of the study, the biometric parameters comprised geometry, wrinkle, volume, skin surface homogeneity and/or skin color variables for 13 defined facial regions. The parameters were classified into genuine/phenotypical parameters and modifiable parameters. Side-specific parameters (right, left) were combined using means or sums, whichever was more meaningful. Face-specific means were calculated for luminance, haemoglobin and melanin parameters as well as regional differences from the face-specific means. For haemoglobin, absolute mean values were stratified by the cheek region and separately for the rest of the face.

Based on the digitally extracted parameters and taking into account their classification, the individual attractiveness and/or youthfulness was calculated. Accordingly, for each individual a model comprising an individual composition and weighting of genuine/phenotypical and modifiable parameters was created.

Additionally, based on the variability of the series of photographs, an optimal value for each modifiable parameter in terms of a high attractiveness and/or youthfulness was determined.

This allowed to determine the individual deviation of each modifiable parameter from the optimum as well as to determine an expected impact of the respective optimal value on the attractiveness and/or youthfulness.

The frequency distribution of each biometric parameter was analysed and presented using histograms for each exposure variable. Outliers of each biometric parameter were defined using Tukey fences, i.e. exposure variable values $>0.75$-quantile$+1.5*$interquartile range (IQR) or $<0.25$-quantile$-1.5*$IQR.

A frequency distribution of ratings per rater stratified by sex was performed to investigate the plausibility of the ratings.

Associations between exposures of interest and facial attractiveness were estimated in a 3-step approach:

(1) Quasi-univariate generalized additive models (GAM) (Wood, 2006) were fitted for each exposure of interest using each subject-rater combination as a single observation. Each model included just one exposure of interest and was adjusted for age and rater, and clustered by subject.

(2) Relevant exposure variables were defined from the quasi-univariate models ($p<0.1$) and included in a multivariate GAM adjusted for age and rater, and clustered by subject.

(3) The final multivariate GAM was identified from (2) by removing exposure variables defined as not modifiable with estimated degrees of freedom $<0.4$.

Optimal values for exposure variables were identified from the estimated association of attractiveness rating with this variable from the multivariate model, but restricted to observed values. For score exposure variables (e.g. wrinkle scores) all observed variable values where considered. For each other modifiable variable, optimal values were determined from the 10 to 90 percent range of the respective variables.

Figure 6:
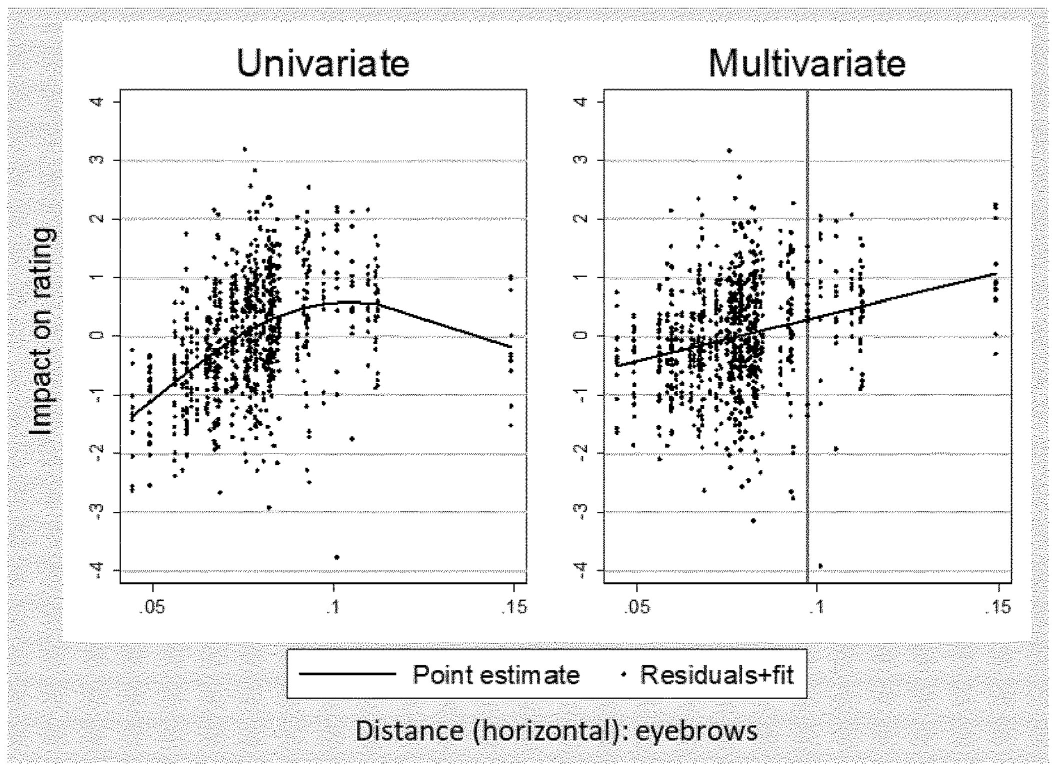
FIGS. 6-7: Diagrams illustrating empirical results relating to the association between biometric parameters of the user's face and the perceived attractiveness in accordance with embodiments of the invention.
Figure 7:
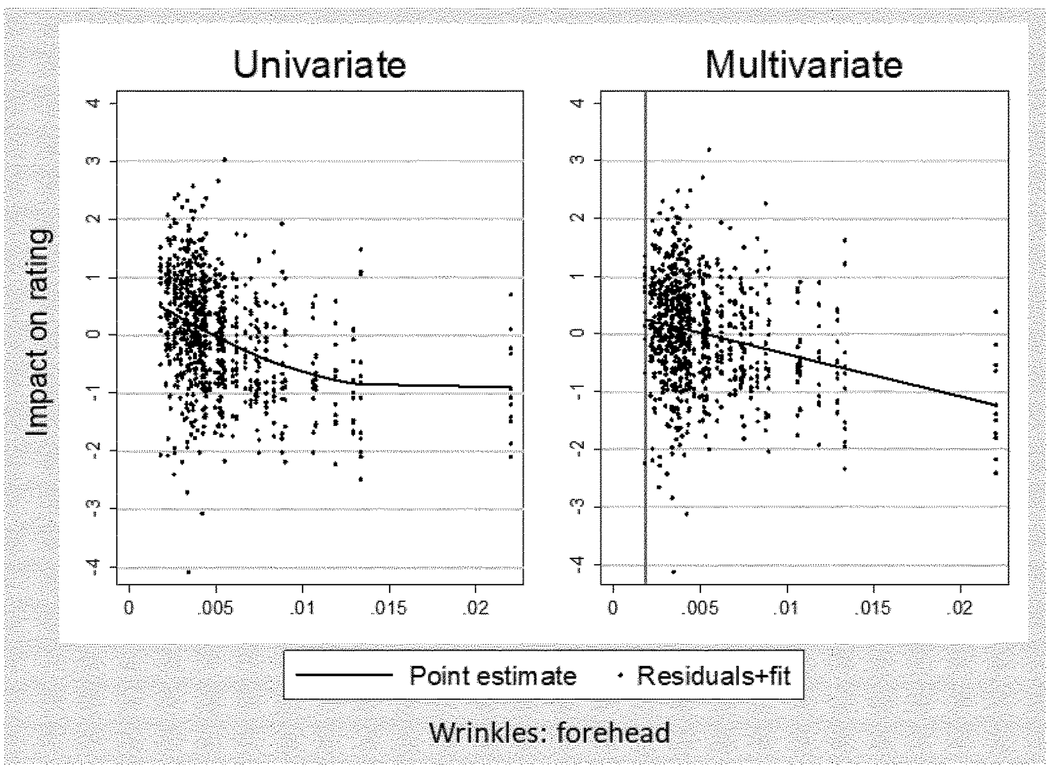

FIG. 6 shows an illustrative example of the association between the biometric parameter "distance of eyebrows" and the attractiveness. The vertical line in the diagram on the right-hand side represents the ideal value. FIG. 7 shows the association between the geometric parameter "forehead wrinkles" and the attractiveness. The position of the ideal value (vertical line) at the left side of the right-hand side diagram denotes a linear relationship.

The impact on attractiveness was calculated for all individuals by changing one exposure variable to its optimal value and fixing all other variables.

The top 3 parameters, i.e. the parameters having the largest impact on the attractiveness and/or youthfulness were selected for each individual and associated with one or more prioritized treatments. In the following, three illustrative examples are provided:

Qualitative Example 1

Melanin (deviation): upper lip
Distance (vertical): lower lip to upper lip
Haemoglobin (mean value): without cheek Qualitative Example 2

Wrinkles: skin
Luminance (deviation): jaw
Distance (vertical): lower lip to upper lip Qualitative Example 3

Luminance (deviation): jaw
Haemoglobin (mean value): without cheek
Distance (vertical): lower lip to upper lip In embodiments of the invention, the one or more biometric parameters may be selected from the group comprising:

at least one geometry-related parameter, such as distance (horizontal): eyes (pupils), distance (vertical): chin to lower lip, distance (vertical): lower lip to upper lip, distance (vertical): upper lip to nose, distance (vertical): nose to eyebrows, distance (vertical): eyebrows to hairline, distance (horizontal): eyes (inner), distance (horizontal): eyes to nose, distance (horizontal): eyebrows, height: lower lip, height: upper lip, width: face (Version A), width: face (Version B), width: eyes, width: chin, width: nose, width: lips, V-shape, mid-face volume, ratio (horizontal): eyebrows, ratio (vertical): eyebrows (1), ratio (vertical): eyebrows (2), ratio (vertical): eyebrows (3), and/or angle: eye axis to eyebrows/inner angle;

at least one wrinkle-related parameter, such as wrinkles: glabella, wrinkles: crow's feet, wrinkles: forehead, wrinkles: upper lip, wrinkles: nasolabial, wrinkles: marionette, wrinkles: infraorbital, wrinkles: eyelids, wrinkles: radial, and/or wrinkles: chin;

at least one homogeneity-related parameter, such as Gabor energy: chin, Gabor energy: upper lip, Gabor energy: nose, Gabor energy: jaw, Gabor energy: cheek, Gabor energy: suborbital, and/or Gabor energy: forehead;

at least one haemoglobin-related parameter, such as haemoglobin: cheek, haemoglobin (mean value): without cheek, haemoglobin (deviation): cheek, haemoglobin (deviation): nose, haemoglobin (deviation): jaw, haemoglobin (deviation): upper lip, haemoglobin (deviation): forehead, and/or haemoglobin (deviation): suborbital;

at least one luminance-related parameter, such as luminance (mean value), luminance (deviation): jaw, luminance (deviation): chin, luminance (deviation): nose, luminance (deviation): upper lip, luminance (deviation): forehead, luminance (deviation): suborbital, and/or luminance (deviation): cheek;

at least one melanin-related parameter, such as melanin (mean value), melanin (deviation): jaw, melanin (deviation): chin, melanin (deviation): nose, melanin (deviation): upper lip, melanin (deviation): forehead, melanin (deviation): suborbital, and/or melanin (deviation): cheek; and/or at least one HSV-related parameter, such as ratio of saturated to total pixels: lower lip, ratio of colorful to total pixels: lower lip, ratio of saturated to total pixels: upper lip, and/or ratio of colorful to total pixels: upper lip.

In embodiments of the invention, to derive a particularly accurate attractiveness score, the one or more biometric parameters may be selected from the group comprising:

at least one geometry-related parameter, such as height: lower lip, mid-face volume, distance (vertical): upper lip to nose, V-shape, width: chin, angle: eye axis to eyebrow inner angle, distance (vertical): lower lip to upper lip, width: lips, height: upper lip, width: eyes, distance (horizontal): eyebrows, ratio (vertical): eyebrows (2), distance (horizontal): eyes (pupils), and/or distance (horizontal): eyes to nose;

at least one wrinkle-related parameter, such as wrinkles: forehead, wrinkles: upper lip, wrinkles: marionette, wrinkles: infraorbital, wrinkles: radial, wrinkles: chin, wrinkles: glabella, and/or wrinkles: nasolabial;

at least one homogeneity-related parameter, such as Gabor energy: nose;

at least one haemoglobin-related parameter, such as haemoglobin (mean): without cheek, and/or haemoglobin: cheek;

at least one luminance-related parameter, such as luminance (deviation): jaw, and/or luminance (mean); and/or at least one melanin-related parameter, such as melanin (deviation): cheek, and/or melanin (deviation) suborbital).

In embodiments of the invention, to derive a particularly accurate youthfulness score, the one or more biometric parameters may be selected from the group comprising:

at least one geometry-related parameter, such as height: lower lip, V-shape, mid-face volume, height: upper lip, distance (vertical): lower lip to upper lip, distance (vertical) upper lip to nose, angle: eye axis to eyebrow inner angle, and/or width: chin;

at least one wrinkle-related parameter, such as wrinkles: glabella, wrinkles: crow's feet; wrinkles: forehead, wrinkles: upper lip, wrinkles: nasolobial, wrinkles: marionette, wrinkles: infraorbital, wrinkles: radial, and/or wrinkles: chin;

at least one homogeneity-related parameter, such as Gabor energy: nose, Gabor energy: upper lip, and/or Gabor energy: cheek;

at least one luminance-related parameter, such as luminance (deviation): cheek; and/or at least one melanin-related parameter, such as melanin (deviation): upper lip, melanin (deviation): cheek, and/or melanin (deviation): jaw.

The following table shows illustrative and non-limiting examples of an association between selected ones of the above-mentioned biometric parameters on estimated attractiveness:

| No. | Description | Modifiable | Mean (SD) | p-value |
|---|---|---|---|---|
| | Geometry | | | |
| 10 | Height: lower lip | Yes | 0.05 (0.00) | 0.0000 |
| 19 | Mid-face volume | Yes | 0.01 (0.00) | 0.0001 |
| | Wrinkles | | | |
| 27 | Wrinkles: forehead | Yes | 0.01 (0.00) | 0.0000 |
| 28 | Wrinkles: upper lip | Yes | 0.01 (0.01) | 0.0000 |
| | Homogeneity | | | |
| 37 | Gabor energy: nose | Yes | 0.10 (0.02) | 0.0000 |
| 39 | Gabor energy: cheek | Yes | 0.08 (0.01) | 0.0339 |
| | Haemoglobin | | | |
| 43 | Haemoglobin (mean): without cheek | Yes | 0.26 (0.03) | 0.0000 |
| 42 | Haemoglobin: cheek | Yes | 0.27 (0.04) | 0.0081 |
| | Luminance | | | |
| 51 | Luminance (deviation): jaw | Yes | −0.06 (0.01) | 0.0002 |
| 50 | luminance (mean) | Yes | 0.51 (0.03) | 0.0058 |
| | Melanin | | | |
| 65 | Melanin (deviation): cheek | Yes | −0.02 (0.01) | 0.0004 |
| 64 | Melanin (deviation): suborbital | Yes | 0.01 (0.02) | 0.0031 |

The following table shows the top 3 modifiable estimated attractiveness drivers for five exemplary individuals:

| Row # | ID | Estimated rating (mean) | Rank | Variable description |
|---|---|---|---|---|
| 1 | 1003 | 3.80 | 1 | Melanin (deviation): forehead |
| 2 | 1003 | 3.80 | 2 | Melanin (deviation): upper lip |
| 3 | 1003 | 3.80 | 3 | Haemoglobin (deviation): suborbital |
| 4 | 1004 | 3.33 | 1 | Melanin (deviation): upper lip |
| 5 | 1004 | 3.33 | 2 | Luminance (deviation): jaw |
| 6 | 1004 | 3.33 | 3 | Haemoglobin (mean value): without cheek |
| 7 | 1005 | 2.83 | 1 | Haemoglobin (mean value): without cheek |
| 8 | 1005 | 2.83 | 2 | Melanin (deviation): upper lip |
| 9 | 1005 | 2.83 | 3 | Luminance (deviation): jaw |
| 10 | 1006 | 5.00 | 1 | Haemoglobin (mean value): without cheek |
| 11 | 1006 | 5.00 | 2 | Luminance (deviation): jaw |
| 12 | 1006 | 5.00 | 3 | Melanin (deviation): upper lip |
| 13 | 1009 | 5.42 | 1 | Melanin (deviation): upper lip |
| 14 | 1009 | 5.42 | 2 | Distance (vertical): lower lip to upper lip |
| 15 | 1009 | 5.42 | 3 | Haemoglobin (mean value): without cheek |

The following table shows illustrative and non-limiting examples of an association between selected ones of the above-mentioned biometric parameters on estimated age/youthfulness:

| No. | Description | Modifiable | Mean (SD) | p-value |
|---|---|---|---|---|
| | Geometry | | | |
| 10 | Height: lower lip | Yes | 0.05 (0.00) | 0.0000 |
| 18 | V-shape | Yes | 1.07 (0.09) | 0.0000 |
| | Wrinkles | | | |
| 25 | Wrinkles: glabella | Yes | 0.01 (0.01) | 0.0000 |
| 26 | Wrinkles: crow's feet | Yes | 0.00 (0.00) | 0.0000 |
| | Homogeneity | | | |
| 37 | Gabor energy: nose | Yes | 0.10 (0.02) | 0.0000 |
| 36 | Gabor energy: upper lip | Yes | 0.08 (0.02) | 0.0015 |
| | Haemoglobin | | | |
| 43 | Haemoglobin (mean): without cheek | Yes | 0.26 (0.03) | 0.0172 |
| 42 | Haemoglobin: cheek | Yes | 0.27 (0.04) | 0.1414 |
| | Luminance | | | |
| 57 | Luminance (deviation): cheek | Yes | 0.03 (0.01) | 0.0053 |
| 50 | Luminance (mean) | Yes | 0.51 (0.03) | 0.0268 |
| | Melanin | | | |
| 62 | Melanin (deviation): upper lip | Yes | −0.01 (0.02) | 0.0000 |
| 65 | Melanin (deviation): cheek | Yes | −0.02 (0.01) | 0.0001 |

The following table shows the top 3 modifiable estimated age/youthfulness drivers for five exemplary individuals:

| Row # | ID | Estimated age (mean) | Rank | Variable description |
|---|---|---|---|---|
| 1 | 1003 | 26.90 | 1 | Mid-face volume |
| 2 | 1003 | 26.90 | 2 | Melanin (deviation): cheek |
| 3 | 1003 | 26.90 | 3 | Wrinkles: chin |
| 4 | 1004 | 62.36 | 1 | Wrinkles: upper lip |
| 5 | 1004 | 62.36 | 2 | Wrinkles: radial |
| 6 | 1004 | 62.36 | 3 | Wrinkles: chin |
| 7 | 1005 | 46.25 | 1 | Wrinkles: radial |
| 8 | 1005 | 46.25 | 2 | Wrinkles: chin |
| 9 | 1005 | 46.25 | 3 | Mid-face volume |
| 10 | 1006 | 27.08 | 1 | Wrinkles: chin |
| 11 | 1006 | 27.08 | 2 | Melanin (deviation): cheek |
| 12 | 1006 | 27.08 | 3 | Melanin (deviation): jaw |
| 13 | 1009 | 24.75 | 1 | Wrinkles: radial |
| 14 | 1009 | 24.75 | 2 | Melanin (deviation): jaw |
| 15 | 1009 | 24.75 | 3 | Mid-face volume |

The following table shows the key drivers (biometric parameters) for attractiveness and/or youthfulness with a user-friendly description and their association with one or more suitable treatment options:

| Key driver | Description | Treatment options |
|---|---|---|
| Distance (vertical): upper lip to nose | Distance nose to upper lip | Filler, surgical intervention, BONT (Botulinum toxin) |
| Distance (vertical): lower lip to upper lip | Ratio upper to lower lip | Filler, surgical intervention |
| Width: chin | Chin width | Filler, BONT, surgical intervention |
| Width: lips | Relative mouth width | Filler, BONT, PDO (Polydioxanon) |
| Wrinkles: eyelids | Upper eyelid wrinkles | BONT, laser, physical procedures, blepharoplastic, PDO |
| Wrinkles: glabella | Frown line | BONT, filler, physical procedures |
| Wrinkles: infraorbital | Lower eyelid wrinkles | Filler, BONT, laser, physical procedures, microneedling/mesotherapy, blepharoplastic, PDO, carboxytherapie |
| Wrinkles: chin | Chin wrinkles | BONT, filler, IPL (Intense Pulsed Light) |
| Wrinkles: crow's feet | Crow's feet | BONT, IPL |
| Wrinkles: marionette | Marionette wrinkles | Filler, PDO, IPL |
| Wrinkles: nasolabial | Nasolabial wrinkles | Filler, PDO, IPL |
| Wrinkles: upper lip | Plisse wrinkles upper lip | BONT, filler, peeling/microderm abrasion, laser |
| Wrinkles: radial | Radial wrinkles at the corner of the mouth | BONT, filler, IPL |
| Wrinkles: forehead | Forehead wrinkles | BONT, peeling/microderm abrasion, RF (Radio Frequency), laser, PDO |
| Gabor Energy: nose | Skin texture of the nose | Peeling/mikroderm abrasion, hydraderm abrasion, laser, IPL, mesolift, carboxytherapy |
| Gabor Energy: upper lip | Skin texture of the upper lip | Peeling/microderm abrasion, hydraderm abrasion, laser, BONT, IPL, mesolift, carboxytherapy |
| Gabor Energy: suborbital | Skin texture of the lower eyelid | Peeling/microderm abrasion, hydraderm abrasion, laser, BONT, physical procedures, IPL, mesolift, carboxytherapy |
| Gabor Energy: cheek | Skin texture of the cheek | IPL, peeling/microderm abrasion, hydraderm abrasion, filler, laser, physical procedures, PDO, mesolift |
| Haemoglobin (mean value): without cheek | Divergent reddish skin tone without considering the cheek | Laser, IPL |
| Haemoglobin: cheek | Divergent reddish skin tone of the cheek | Laser, IPL |
| Luminance (deviation): jaw | Color harmony jaw | Make up, peeling, microneedling/mesotherapy, laser |
| Luminance (deviation): cheek | Color harmony cheek | Make up, peeling, Microneedling/Mesotherapie, Laser |
| Luminance (mean value) | Color harmony mean value | Make Up, Peeling, Mikroneedling/mesotherapy, laser |
| Melanin (deviation): jaw | Divergent brownish skin tone jaw | Peeling, microneedling (supportive treatment)/mesotherapy, laser, IPL |
| Melanin (deviation): chin | Divergent brownish skin tone chin | Peeling, microneedling (supportive treatment)/mesotherapy, laser, IPL |
| Melanin (deviation): upper lip | Divergent brownish skin tone upper lip | Peeling, microneedling (supportive treatment)/mesotherapy, laser, IPL |
| Melanin (deviation): forehead | Divergent brownish skin tone forehead | Peeling, microneedling (supportive treatment), laser, IPL |
| Melanin (deviation): suborbital | Divergent brownish skin tone suborbital | Peeling, microneedling (supportive treatment), laser, IPL |
| Melanin (deviation): cheek | Divergent brownish skin tone sheek | Peeling, microneedling (supportive treatment)/mesotherapy, laser, IPL |

-continued

| Key driver | Description | Treatment options |
|---|---|---|
| Mid-face volume | Volume of the mid-face/ cheeks, eye channel | Filler, lipolyse, RF, ultrasonic |
| V-shape | V-shaped face | Filler, BONT, RF, ultrasonic, PDO, surgical procedures |
| Angle: eye axis to eyebrow/inner angle | Eyebrow arch | RF, surgical procedures, PDO |

Generally speaking, the key drivers, i.e. biometric parameters, may represent deficiencies of the user's face/body part(s). The more severe the deficiency, the lower may the score of the physiological characteristic(s) be and/or the higher the optimization potential may be.

In certain studies, the following biometric parameters had the most significant impact on attractiveness: haemoglobin: cheek, wrinkles: upper lip, wrinkles: infraorbital, haemoglobin (mean): without cheek, wrinkles: radial.

In certain studies, the following biometric parameters had the most significant impact on youthfulness: wrinkles: upper lip, haemoglobin (means): without cheeks, melanin (deviation): jaw, luminance (mean), melanin (deviation): cheek.

Thus, in certain embodiments of the invention, the above or any subset of the above biometric parameters may be selected.

Machine Learning Implementation

Generally speaking, the quality of the machine learning model depends on the training data sets (e.g. images), features extracted from the images (e.g. the biometric parameters), target values (e.g. expert ratings of attractiveness) and/or modelling methods. The data sets are suitable if they correspond in terms of composition and quality to those which will be used later during runtime. The features are suitable if they represent characteristics of the data which are relevant for the estimation and at the same time suppress random correlations. The target values are suitable if they are as unambiguous/objective as possible. For example, it is meaningful to use the consent of the experts (e.g. intra class correlation ICC 2.1) to check whether a model can yield similar results. Statistical-aesthetic modelling techniques are an important aspect of high-quality data-based modelling. It is important to adequately choose the model complexity. Therefore, it is advisable to start with simple methods and then to get more complex (assuming usable data). In particular, overfitting must be avoided, which can be achieved by way of suitable test methods (e.g. hold-out test set, cross validation).

The number of data sets (in the present case: images) is relevant. Generally speaking, the more images the better the results will be. Assuming that the data sets are representative and contain relevant features, "simple" methods can be modelled also with fewer data sets in order to estimate overall attractiveness and the impact of individual biometric parameters. Prior results have shown high clinical plausibility. Starting from such models, different methods can be used to increase the model complexity, and it can be checked whether the new models improve the estimation quality. There is no general rule of thumb for the necessary amount of data sets for a given modelling method. However, one can assume that the precision of the clinically plausible predictors for overall attractivity and youthfulness increases with increasing number of images.

For example, in the case of highly complex features (which describe specific aspects of the face), comparatively simple models (e.g. linear regression) can result in good estimates. Here, a large part of the problem complexity is already implemented in the features.

Using deep neural networks (DNNs), oftentimes the step of feature extraction is connected with the step of model building. This means that the feature representation and the estimation model are trained simultaneously. Therefore, DNNs require a very large data set since in the simplest case the model starts "from zero". In the literature and in practice, methods such as transfer learning have prevailed to this end. Using transfer learning, the model can be pre-trained with a publicly available data set (for a similar problem domain). The pre-trained model is then later refined using only relatively few examples from the specific problem domain (so-called few-shot or on-shot learning).

The present techniques for estimating attractiveness, youthfulness and/or age of embodiments of the invention (via the facial contour detection and the identification of relevant features) already embody the characteristics of hundreds of images and the experience of human experts, as well as the learnings from countless publications. A DNN would have to learn all this from examples first.

Generally speaking, neural networks are very flexible in their complexity and can define some dozens up to millions of parameters. Simple models (with few parameters) require only less data.

Experiments have shown that e.g. 500 images are not enough to estimate the attractiveness and/or youthfulness directly from images of the face, but that an area of roughly 10,000 images could be sufficient. In the case of the present invention (with complex, manually developed features), fewer images can suffice for a stable estimation.

It is advisable in both cases to confirm the validity of the model estimation by way of test images (which have not been used for building the model).

The above illustrates why the presently techniques employed in embodiments of the invention are very different from classic deep learning approaches in the areas of image classification, clustering or text analysis.

FURTHER EMBODIMENTS

Further embodiments are disclosed as follows:

1. A computer-implemented method for identifying of an objective attractiveness and/or juvenileness index and prioritization of patient treatment options for improvement of a juvenile and attractive appearance based on an analysis of landmarks, comprising:
   retrieving the results of measurement of one or more digital photos of the patient (face, body, . . . ),
   identifying a combination of treatments associated with any of the set of one or more landmarks via identifying rules relating the treatments to landmarks, the rules being stored in a self-learning treatment-information database, the rules corresponding to one or several observations of an objective outcome after a treatment, determining the objective attractiveness- and/or juvenileness index for the retrieved measurement based on landmarks and determining changes in the objective attractiveness—and/or juvenileness index if one or more of the identified treatments would be applied, determining the impact for each of the identified combined and prioritized (plurality of) treatments based on the determined change of the objective attractiveness and/or juvenileness index, wherein the landmarks are different rated, and ordering the identified plurality of treatments according to the determined impact to provide a treatment option and a prioritization of treatments for increasing the objective attractiveness and/or youthfulness index for the patient, on objective grounds, characterized in that the score is computed by selecting one or more of the landmarks that are related to skin, wrinkles, color, volume, proportions, geometry.

2. Method according to embodiment 1, characterized in that an ordered list of treatment options is generated, wherein treatment options are ordered based on their determined impact on the objective attractiveness- and/or juvenileness index beginning from the treatment with the highest impact and outputting of the ordered list.

3. Method according to embodiment 2, characterized in that the first treatment is selected from the ordered list and the patient is treated accordingly.

4. Method for identification of individualized, prioritized treatment plans to optimize attractiveness and youthfulness of human faces and/or body based on objective analysis of related landmarks using validated algorithms.

The systems and methods described herein may be embodied by a computer program or a plurality of computer programs, which may exist in a variety of forms both active and inactive in a single computer system or across multiple computer systems. For example, they may exist as software program(s) comprised of program instructions in source code, object code, executable code or other formats for performing some of the steps. Any of the above may be embodied on a computer readable medium, which include storage devices and signals, in compressed or uncompressed form.

The term "computer" refers to any electronic device comprising a processor, such as a general-purpose central processing unit (CPU), a specific purpose processor or a microcontroller. A computer is capable of receiving data (an input), of performing a sequence of predetermined operations thereupon, and of producing thereby a result in the form of information or signals (an output). Depending on context, the term "computer" will mean either a processor in particular or can refer more generally to a processor in association with an assemblage of interrelated elements contained within a single case or housing.

A mobile device can be any type of portable electronic device, including a cellular telephone, a Personal Digital Assistant (PDA), smartphone, tablet, etc. The mobile device can comprise a display, a Global Positioning System (GPS) module, a Global Navigation Satelite System (GLONASS) module, a compass, one or more cameras and various other input/output (I/O) components.

As used herein, a "computer-readable medium" or "storage medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

The invention claimed is:

1. A computer-implemented body part analysis method, comprising:

an image acquisition step, comprising obtaining one or more digital images of at least one body part of a user, in particular the user's face, captured by an image capturing device;

an image processing step, comprising detecting one or more biometric parameters of the at least one body part in the captured one or more digital images; and an evaluation step, comprising determining a score for each of one or more physiological characteristics of the at least one body part based on the detected one or more biometric parameters, wherein the one or more digital images comprise a first digital image with a frontal view of the user's face;

wherein the one or more digital images further comprise a second digital image with a lateral view of the user's face;

wherein the one or more digital images further comprise a third digital image with a facial expression different from the facial expression in the first digital image;

wherein the facial expression in the third digital image is a smiling facial expression or a frowning facial expression;

wherein the facial expression in the third digital image is a smiling facial expression and wherein the one or more digital images further comprise a fourth digital image with a frowning facial expression;

wherein the second digital image with the lateral view shows the user's face approximately at an angle between 20 and 70 degrees;

wherein the image acquisition step further comprises providing instructions to the user for adjusting a lighting, a position of the user's face relative to the image capturing device, a distance of the user's face to the image capturing device and/or an orientation of the user's face relative to the image capturing device; and wherein the step of providing instructions comprises displaying text, symbols and/or visual indications, such as one or more leading lines, on a display associated with the image capturing device.

2. The computer-implemented body part analysis method of claim 1, wherein the one or more biometric parameters are selected from the group comprising:

skin texture, in particular relating to the nose, upper lip, suborbital area and/or cheek; wrinkles, in particular relating to the eye lids, glabella, infraorbital area, chin, crow's feet, marionette wrinkles, nasolabial area, upper lip, radial area and/or forehead;

color, in particular relating to haemoglobin, luminance and/or melanin;

volume, in particular relating to the cheek(s), eye groove and/or midface region; proportions, in particular relating to the distance between nose, upper lip and/or lower lip, the chin width, the lip width and/or the V-shape; and/or geometry, in particular relating to the eyebrow arch.

3. The computer-implemented body part analysis method of claim 1, wherein the one or more physiological characteristics comprise the skin firmness, the skin smoothness, the skin elasticity, the perceived age, the attractiveness and/or the youthfulness of the user.

4. The computer-implemented body part analysis method of claim 1, wherein at least one of:

(a) the first digital image with the frontal view of the user's face comprises a neutral facial expression;

(b) the second digital image with the lateral view of the user's face comprises a neutral facial expression;

(c) the third digital image comprises a frontal view of the user's face;

(d) wherein the fourth digital image comprises a frontal view of the user's face;

wherein the angle is between 30 and 60 degrees; or (e) wherein the angle is at approximately 45 degrees.

5. The computer-implemented body part analysis method of claim 1, wherein the one or more digital images are captured using a mobile device, in particular a smartphone, or wherein the one or more digital images are captured using an electronic device incorporated in a smart mirror.

6. The computer-implemented body part analysis method of claim 1, wherein the evaluation step is performed using at least one statistical classifier which is configured to map one or more biometric features to a score for one or more physiological characteristics of the at least one body part;

wherein preferably a first statistical classifier is configured to map a first predefined set of biometric features to an attractiveness score and preferably a second statistical classifier is configured to map a second predefined set of biometric features to a youthfulness score, wherein the first and second predefined sets of biometric features preferably overlap partially;

wherein the first predefined set comprise at least one biometric parameter relating to color, in particular relating to haemoglobin, luminance and/or melanin;

wherein the second predefined set comprises at least one biometric parameter relating to wrinkles, in particular relating to the eye lids, glabella, infraorbital area, chin, crow's feet, marionette wrinkles, nasolabial area, upper lip, radial area and/or forehead.

7. The computer-implemented body part analysis method of claim 6, wherein the at least one statistical classifier has been trained using a training data set comprising a plurality of images of human faces, a selection of one or more biometric parameters and/or a score for each of one or more physiological characteristics; and/or wherein the statistical classifier has been trained and/or pre-trained using a publicly available data set, such as SCUT-FBP.

8. The computer-implemented body part analysis method of claim 7, wherein a training data set comprises a plurality of images of human faces, a selection of one or more biometric parameters, and/or a score for each of one or more physiological characteristics.

9. The computer-implemented body part analysis method of claim 8 further comprising training the at least one statistical classifier using the training data set.

10. The computer-implemented body part analysis method of claim 6, wherein the at least one statistical classifier is an artificial neural network, in particular a deep neural network.

11. The computer-implemented body part analysis method of claim 1, further comprising the steps of displaying the one or more scores on a display associated with the image capturing device; and recommending, to the user, one or more treatments to improve the score associated with the one or more physiological characteristics;

wherein the one or more recommended treatments are ranked by their predicted impact on improving the score associated with the one or more physiological characteristics.

12. The computer-implemented body part analysis method of claim 1, further comprising the step of displaying an estimated change of the one or more scores after application of the recommended one or more treatments.

13. An apparatus comprising means for carrying out the method of claim 1.

14. A non-transitory computer-readable storage medium storing a computer program comprising instructions which, when the program is executed by a computer, cause the computer to carry out the method of claim 1.

15. A non-transitory computer-readable storage medium comprising instructions which, when executed by a computer, cause the computer to carry out the method of claim 1.

* * * * *